US009408528B2

(12) United States Patent
Kudo et al.

(10) Patent No.: US 9,408,528 B2
(45) Date of Patent: Aug. 9, 2016

(54) STEREOSCOPIC ENDOSCOPE SYSTEM

(71) Applicant: Olympus Corporation, Tokyo (JP)

(72) Inventors: Masahiro Kudo, Hino (JP); Hironori Sakurai, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 92 days.

(21) Appl. No.: 14/504,054

(22) Filed: Oct. 1, 2014

(65) Prior Publication Data

US 2015/0085074 A1 Mar. 26, 2015

Related U.S. Application Data

(63) Continuation of application No. PCT/JP2013/080504, filed on Nov. 12, 2013.

(30) Foreign Application Priority Data

Mar. 29, 2013 (JP) .................................. 2013-073600

(51) Int. Cl.
*H04N 15/00* (2006.01)
*H04N 13/00* (2006.01)
*A61B 1/04* (2006.01)
*A61B 1/00* (2006.01)
(Continued)

(52) U.S. Cl.
CPC ......... *A61B 1/00193* (2013.01); *A61B 1/00009* (2013.01); *H04N 13/0022* (2013.01); *H04N 13/0207* (2013.01); *H04N 13/0239* (2013.01); *H04N 13/0402* (2013.01); *H04N 7/18* (2013.01); *H04N 13/004* (2013.01); *H04N 13/0434* (2013.01); *H04N 2013/0081* (2013.01)

(58) Field of Classification Search
CPC ........... A61B 1/00193; G02B 23/2415; H04N 13/0055; H04N 13/0203
USPC .......................................................... 348/45
See application file for complete search history.

(56) References Cited

FOREIGN PATENT DOCUMENTS

| EP | 2424253 A2 | 2/2012 |
|---|---|---|
| JP | A-2001-78174 | 3/2001 |

(Continued)

OTHER PUBLICATIONS

Partially Translated Office Action issued in Japanese Application No. 2014-544286 mailed Nov. 4, 2014.

(Continued)

*Primary Examiner* — Mehrdad Dastouri
*Assistant Examiner* — Kristin Dobbs
(74) *Attorney, Agent, or Firm* — Oliff PLC

(57) ABSTRACT

A stereoscopic endoscope system includes: a corresponding point detection section that detects a position of an object in each of an image for the right eye and an image for the left eye based on right and left video signals; a horizontal position moving section that moves, based on a parallax between the image for the right eye and the image for the left eye and depth information of a stereoscopic video which are obtained from the detected positions, horizontal positions of the right and left video signals, by an amount of the parallax, respectively in directions determined according to the depth information; a vertical/horizontal inversion section that vertically and horizontally inverts the right and left video signals whose horizontal positions have been moved; and a stereoscopic signal combining section that combines the right and left video signals subjected to the vertical/horizontal inversion, and generates a stereoscopic video signal.

4 Claims, 11 Drawing Sheets

(51) Int. Cl.
*H04N 13/02* (2006.01)
*H04N 13/04* (2006.01)
*H04N 7/18* (2006.01)

(56) References Cited

FOREIGN PATENT DOCUMENTS

| JP | A-2001-272760 | 10/2001 |
| JP | A-2006-284877 | 10/2006 |
| JP | A-2010-206495 | 9/2010 |
| WO | WO 2004/084559 A1 | 9/2004 |

OTHER PUBLICATIONS

International Search Report issued in International Application No. PCT/JP2013/080504 mailed Feb. 10, 2014 (with translation).

May 19, 2016 Extended European Search Report issued in European Application No. 13879902.8.

STEREOSCOPIC ENDOSCOPE SYSTEM

CROSS REFERENCE TO RELATED APPLICATION

This application is a continuation application of PCT/JP2013/080504 filed on Nov. 12, 2013 and claims benefit of Japanese Application No. 2013-073600 filed in Japan on Mar. 29, 2013, the entire contents of which are incorporated herein by this reference.

BACKGROUND OF THE INVENTION

1. Field of the Invention

The present invention relates to a stereoscopic endoscope system and more particularly to a stereoscopic endoscope system that displays a stereoscopic video.

2. Description of the Related Art

Conventionally, endoscopes have been widely used in medical fields and other fields. In addition, there is a case where endoscopic surgeries are performed under the observation using an endoscope by forming small holes through which the endoscope is inserted to treat a diseased part and the like in the body cavity of a patient. Among such endoscopic surgeries, in an endoscopic surgery of the chest, for example, a surgeon and an assistant face each other to perform the surgery. When a surgeon and an assistant perform an endoscopic surgery while facing each other, a vertically and horizontally inverted video is required in some cases, as described with reference to the FIG. 12 below.

FIG. 12 illustrates an example of a layout of an endoscopic surgery of the chest. As shown in FIG. 12, when a surgeon 100 and an assistant 101 perform an endoscopic surgery of the chest, the surgeon and the assistant perform the surgery facing each other with a patient 102 therebetween. An endoscope 103 is inserted in the body cavity of the patient 102, and an endoscopic image picked up with the endoscope 103 is displayed on a surgeon's monitor 104 and an assistant's monitor 105.

The endoscope 103 is inserted in the body cavity of the patient 102 in the direction coincident with the field of view direction of the surgeon 100. Therefore, the up, down, right, and left directions of the endoscopic image observed by the surgeon 100 on the surgeon's monitor 104 are coincident with the up, down, right, and left directions of forceps 106, 107 which are actually operated by the surgeon 100. As a result, the forceps 106 which is operated by the surgeon 100 with the right hand is located on the lower right side in a screen 104a of the surgeon's monitor 104, and the forceps 107 which is operated by the surgeon 100 with the left hand is located on the lower left side in the screen 104a of the surgeon's monitor 104. Therefore, the forceps 106, 107 in the screen 104a of the surgeon's monitor 104 move in the same directions as the directions in which the surgeon 100 operates the forceps with the right hand and the left hand.

On the other hand, since the assistant 101 faces the surgeon 100, the up, down, right, and left directions of the forceps viewed from the assistant 101 in the space in the body cavity are opposite to the up, down, right, and left directions of the forceps viewed from the surgeon 100. However, since the endoscopic image displayed on the assistant's monitor 105 is the same as the endoscopic image displayed on the surgeon's monitor 104, the up, down, right, and left directions of the image are the same as those of the image viewed from the surgeon 100. As a result, a forceps 108 operated by the assistant 101 with the right hand is located on the upper left side in a screen 105a of the assistant's monitor 105 and a forceps 109 operated by the assistant 101 with the left hand is located on the upper right side in the screen 105a of the assistant's monitor 105. Therefore, the forceps 108 and 109 in the screen 105a of the assistant's monitor 105 move in the directions opposite to the up, down, right, and left directions in which the assistant 101 operates the forceps with the right hand and the left hand.

The assistant 101 is required to operate the forceps 108 and 109 in the directions opposite to the up, down, right, and left directions in the actual operational sense so as to move the forceps 108 and 109 in the screen 105a of the assistant's monitor 105 to appropriate positions. Such an operation leads to extremely poor operational performance for the assistant 101. Therefore, in the surgery layout as shown in FIG. 12, a vertically and horizontally inverted video is required to be displayed on the assistant's monitor 105, in order to improve the operational performance for the assistant 101.

In view of the above, Japanese Patent Application Laid-Open Publication No. 2001-272760, for example, discloses a surgery microscope system for displaying on an assistant's monitor an image obtained as a result of vertically and horizontally inverting the image displayed on the surgeon's monitor.

Incidentally, in recent years, a stereoscopic endoscope system capable of presenting a stereoscopic video including depth information to observers (surgeon and assistant) has been developed. The stereoscopic endoscope system includes a stereoscopic endoscope and a stereoscopic monitor. The stereoscopic endoscope picks up two endoscopic images having parallax, for the right eye and the left eye, and the stereoscopic monitor enables video signals for the right eye and video signals for the left eye, which have been picked up with the stereoscopic endoscope, to be respectively observed only with the corresponding right eye and left eye of the observer. According to such a system, the observer can grasp the depth information, which enables the observer to visually confirm the near-far relationship among tissues in the body cavity and treatment instruments, etc., the images of which have been picked up with the stereoscopic endoscope. As a result, the operational performance of the treatment instruments, etc., is improved.

Also in the case where such a stereoscopic endoscope system is applied to the layout of the endoscopic surgery of the chest as shown in FIG. 12, the operational performance for the assistant must be improved by displaying a vertically and horizontally inverted image on the assistant's monitor.

SUMMARY OF THE INVENTION

A stereoscopic endoscope system according to one aspect of the present invention comprises: a stereoscopic endoscope that obtains right and left image pickup signals; a stereoscopic monitor that displays a stereoscopic video corresponding to right and left video signals obtained as a result of predetermined video signal processing performed on the right and left image pickup signals that are obtained with the stereoscopic endoscope; a corresponding point detection section that detects a position of an object in each of an image for the right eye and an image for the left eye based on the inputted right and left video signals; a horizontal position moving section that moves, based on a parallax between the image for the right eye and the image for the left eye and depth information of the stereoscopic video, horizontal positions of the right and left video signals, by an amount of the parallax, respectively in directions determined according to the depth information, the parallax and the depth information being obtained based on the position in the image for the right eye and the position in the image for the left eye that are outputted from the corresponding point detection section; a vertical/horizontal inversion section that vertically and horizontally inverts the right and left video signals whose horizontal positions have been moved by the horizontal position moving section; and a stereoscopic signal combining section that combines the right and left video signals subjected to the vertical/horizontal inversion by the vertical/horizontal inversion section, and generates a stereoscopic video signal.

BRIEF DESCRIPTION OF THE DRAWINGS

FIG. 7A illustrates a configuration of a vertical/horizontal inversion section 33.

FIG. 7B illustrates the configuration of the vertical/horizontal inversion section 33.

FIG. 11 illustrates a detailed configuration of a stereoscopic monitor 4a.

DETAILED DESCRIPTION OF THE PREFERRED EMBODIMENTS

Hereinafter, embodiments of the present invention will be described with reference to drawings.

First Embodiment

First, with reference to FIG. 1, description will be made on a stereoscopic endoscope system according to a first embodiment of the present invention.

Figure 1:
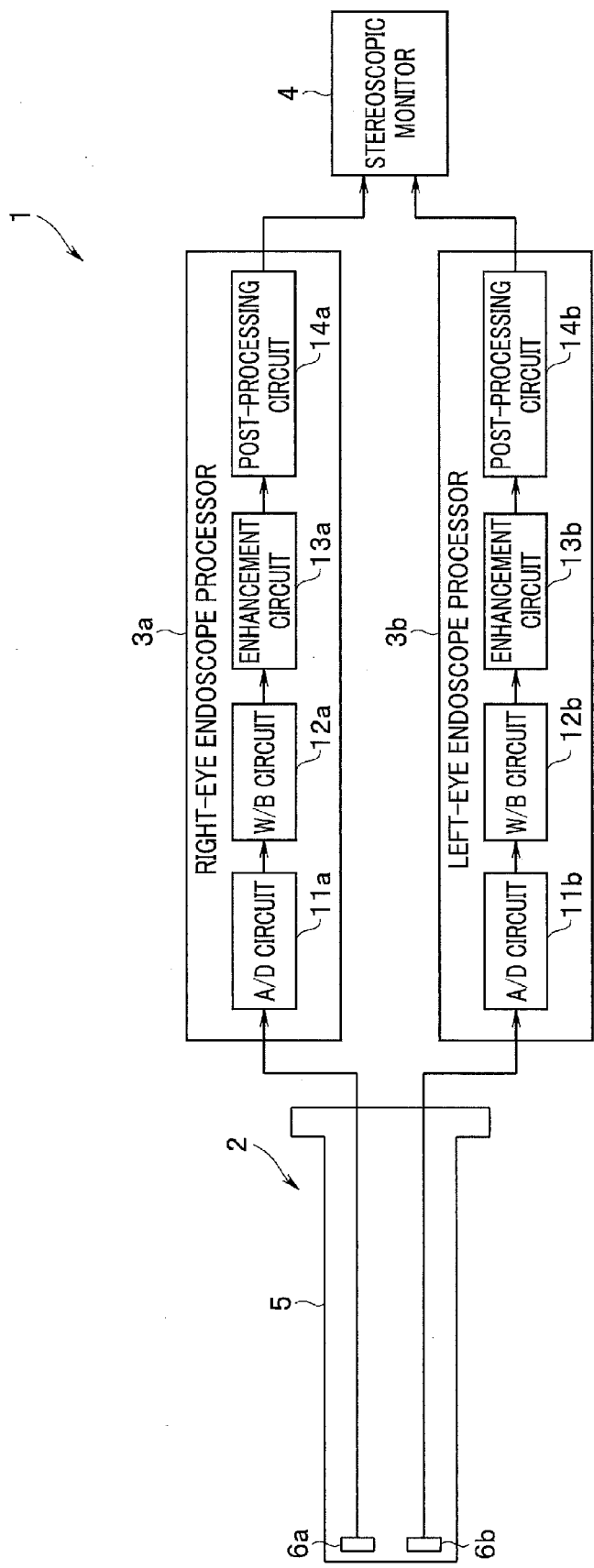
FIG. 1 is a configuration diagram showing a configuration of a stereoscopic endoscope system according to a first embodiment of the present invention.

FIG. 1 is a configuration diagram showing a configuration of the stereoscopic endoscope system according to the first embodiment of the present invention.

As shown in FIG. 1, the stereoscopic endoscope system 1 includes: a stereoscopic endoscope 2 that picks up an image of an object in a living body and outputs image pickup signals for the left eye and image pickup signals for the right eye; a right-eye endoscope processor 3a that converts the image pickup signals for the right eye into video signals for the right eye to output the video signals for the right eye; a left-eye endoscope processor 3b that converts image pickup signals for the left eye into video signals for the left eye to output the video signals for the left eye; and a stereoscopic monitor 4 that generates a stereoscopic video from the video signals for the right eye and the video signals for the left eye to display the generated stereoscopic video. Note that the right-eye endoscope processor 3a and the left-eye endoscope processor 3b may be configured as an integrated endoscope processor.

The stereoscopic endoscope 2 has an insertion portion 5 configured to be insertable inside the living body. The insertion portion 5 includes, at the distal end thereof, two image pickup devices such as CCDs, i.e., a right-eye image pickup device 6a and a left-eye image pickup device 6b in the present embodiment. The stereoscopic endoscope 2 obtains the image pickup signals for the right eye and the image pickup signals for the left eye (right and left image pickup signals) with the right-eye image pickup device 6a and the left-eye image pickup device 6b, respectively. The image pickup signals for the right eye obtained with the right-eye image pickup device 6a are inputted to the right-eye endoscope processor 3a, and the image pickup signals for the left eye obtained with the left-eye image pickup device 6b are inputted to the left-eye endoscope processor 3b.

The right-eye endoscope processor 3a includes an A/D circuit 11a, a white balance (hereinafter, abbreviated as W/B) circuit 12a, an enhancement circuit 13a, and a post-processing circuit 14a.

The A/D circuit 11a converts the image pickup signals for the right eye outputted from the right-eye image pickup device 6a, from an analog signal to a digital signal, and outputs the digital signal to the W/B circuit 12a. The W/B circuit 12a performs white balance processing on the output signal outputted from the A/D circuit 11a, to output the signal subjected to the white balance processing to the enhancement circuit 13a. The enhancement circuit 13a performs contour enhancement processing for enhancing the contour of the object on the output signal outputted from the W/B circuit 12a, to output the signal subjected to the contour enhancement processing to the post-processing circuit 14a. The post-processing circuit 14a converts the output signal outputted from the enhancement circuit 13a into a video signal in SDI (Serial Digital Interface), DVI (Digital Visual Interface), or the like, to generate the video signals for the right eye.

The left-eye endoscope processor 3b has the same configuration as that of the right-eye endoscope processor 3a, and includes an A/D circuit 11b, a W/B circuit 12b, and an enhancement circuit 13b, and a post-processing circuit 14b.

The image pickup signals for the left eye outputted from the left-eye image pickup device 6b pass through the A/D circuit 11b, the W/B circuit 12b, the enhancement circuit 13b, and the post-processing circuit 14b, and thereby the video signals for the left eye are generated. The video signals for the right and left eyes thus generated are inputted to the stereoscopic monitor 4. The stereoscopic monitor 4 displays a stereoscopic video corresponding to the video signals for the right and left eyes thus subjected to predetermined video signal processing.

Figure 2:
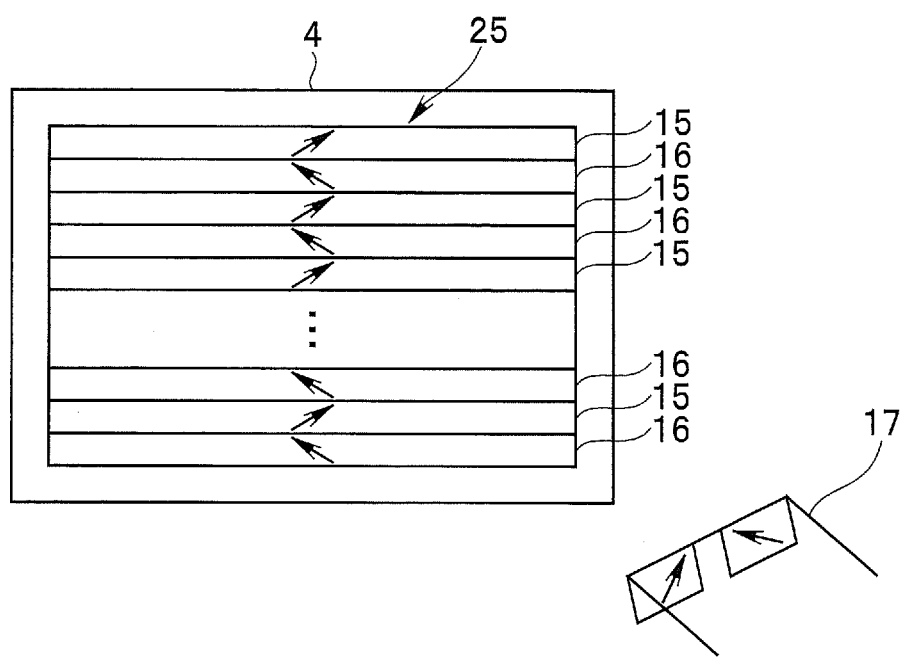
FIG. 2 illustrates an appearance configuration of a stereoscopic monitor 4.

FIG. 2 illustrates an appearance configuration of a stereoscopic monitor 4. As shown in FIG. 2, the stereoscopic monitor 4 is provided with a stereoscopic display panel 25 (See FIG. 3 to be described later). Polarization plates 15, 16, which have different polarization directions, are pasted alternately line by line on the stereoscopic display panel 25, and an image for the left eye and an image for the right eye are assigned alternately line by line, to be displayed.

An observer can observe the video obtained with the stereoscopic endoscope 2 as a stereoscopic video by wearing a pair of polarizing glasses 17 having polarization directions respectively coincident with the polarization directions of the respective polarization plates 15, 16 pasted on the stereoscopic display panel 25 of the stereoscopic monitor 4.

Figure 3:
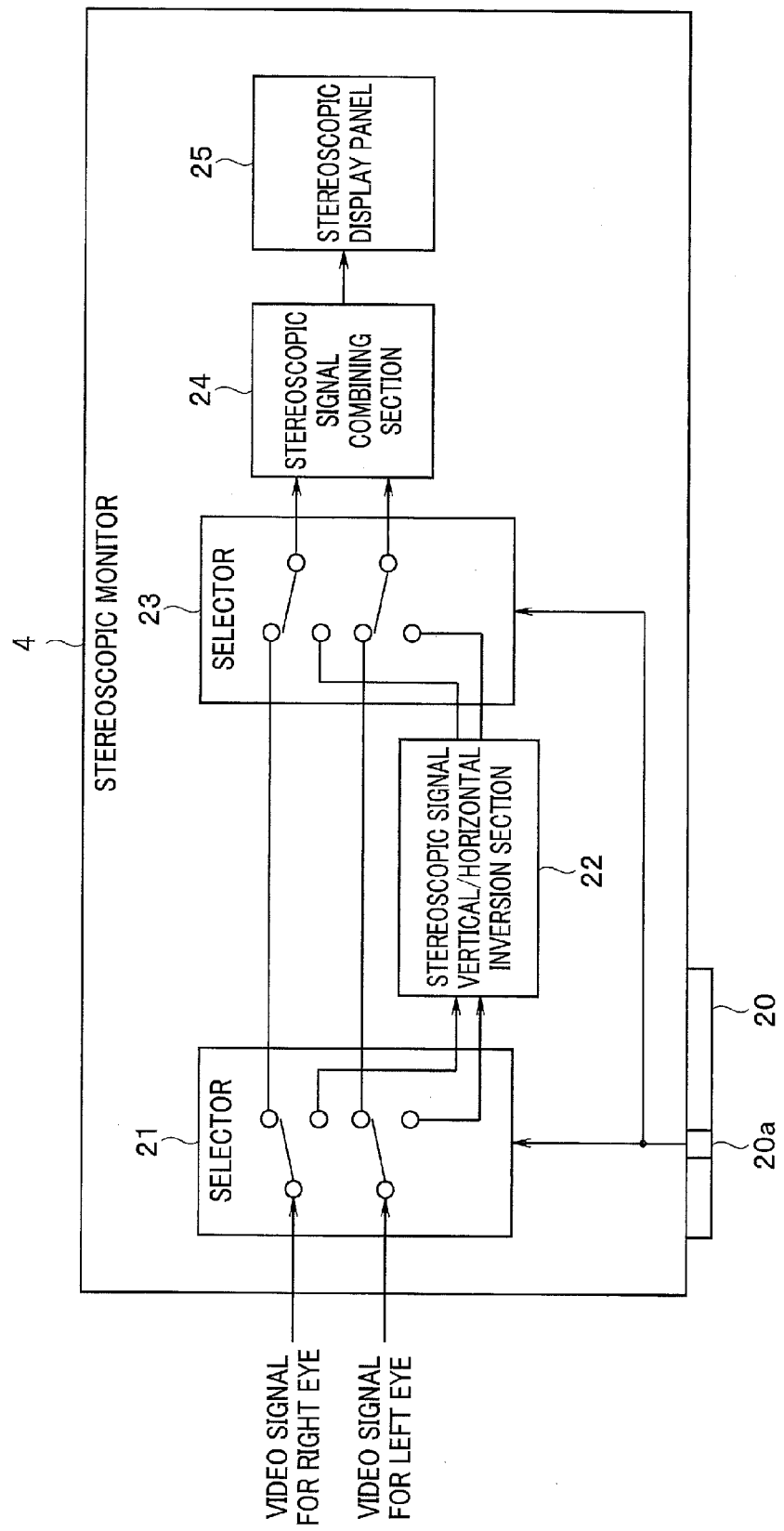
FIG. 3 illustrates a detailed configuration of the stereoscopic monitor 4.

Next, description will be made on the detailed configuration of the stereoscopic monitor 4. FIG. 3 illustrates the detailed configuration of the stereoscopic monitor 4.

As shown in FIG. 3, the stereoscopic monitor 4 includes a front switch 20, a selector 21, a stereoscopic signal vertical/horizontal inversion section 22, a selector 23, a stereoscopic signal combining section 24, and a stereoscopic display panel 25.

The front switch 20 is provided with a vertical/horizontal inversion switch 20a for switching whether or not to perform vertical/horizontal inversion processing on the video signals for the right and left eyes. The observer turns on or off the vertical/horizontal inversion switch 20a, to thereby cause the selectors 21 and 23 to switch the processing paths regarding whether or not to perform the vertical/horizontal inversion processing.

Specifically, when the vertical/horizontal inversion switch 20a is OFF, the processing path is switched to a normal processing path in which the vertical/horizontal inversion processing is not performed. The selector 21 performs switching so as to output the video signals for the right and left eyes to the selector 23. Then, the selector 23 performs switching so as to output the video signals for the right and left eyes outputted from the selector 21 to the stereoscopic signal combining section 24.

On the other hand, when the vertical/horizontal inversion switch 20a is ON, the processing path is switched to the processing path in which the vertical/horizontal inversion processing is performed. The selector 21 performs switching so as to output the video signals for the right and left eyes to the stereoscopic signal vertical/horizontal inversion section 22. Then, the selector 23 performs switching so as to output the video signals for the right and left eyes subjected to the vertical/horizontal inversion processing by the stereoscopic signal vertical/horizontal inversion section 22 to the stereoscopic signal combining section 24. Note that a description will be made on the configuration of the stereoscopic signal vertical/horizontal inversion section 22 later.

Thus, the stereoscopic signal combining section 24 receives the video signals for the right and left eyes which are not subjected to the vertical/horizontal inversion processing, or the video signals for the right and left eyes subjected to the vertical/horizontal inversion processing. The stereoscopic signal combining section 24 combines the received video signals for the right and left eyes to generate a stereoscopic video signal, and outputs the generated stereoscopic video signal to the stereoscopic display panel 25. Now, description will be made on the combining processing in the stereoscopic signal combining section 24 with reference to FIG. 4.

Figure 4:
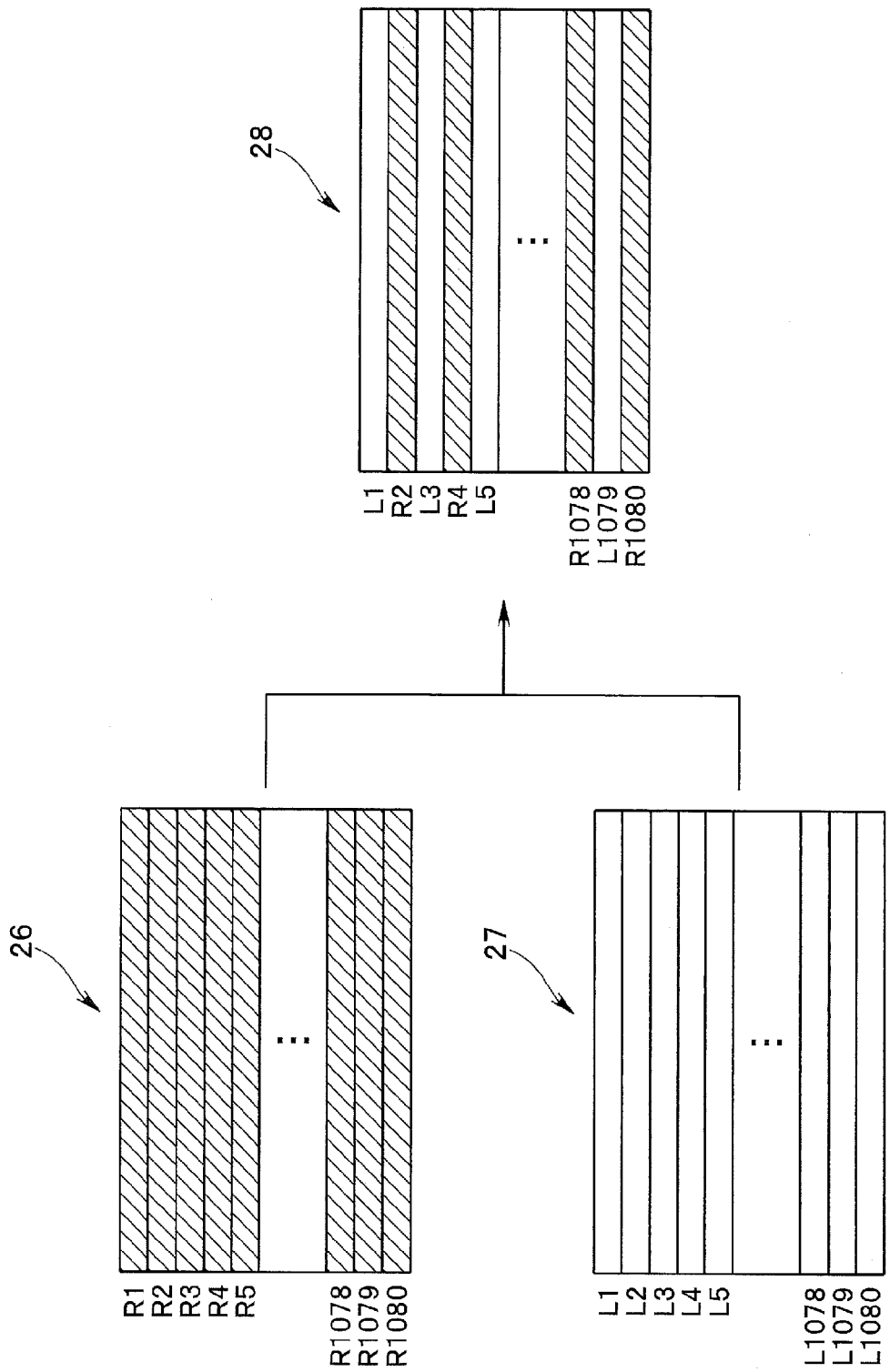
FIG. 4 illustrates combining processing performed by a stereoscopic signal combining section 24.

FIG. 4 illustrates the combining processing performed by the stereoscopic signal combining section 24. As shown in FIG. 4, the stereoscopic signal combining section 24 combines the signals in a line-by-line stereoscopic video format, i.e., received video signals for the right eye 26 and video signals for the left eye 27 into a signal in which left-eye signals and right-eye signals are alternately arranged line by line, to generate a combined signal 28.

Specifically, the stereoscopic signal combining section 24 generates a combined signal 28 including a line L1 of video signal for the left eye 27, a line R2 of the video signal for the right eye 26, a line L3 of the video signal for the left eye 27, . . . , and a line R1080 of the video signal for the right eye 26. The combined signal 28 obtained as a result of the combining is outputted to the stereoscopic display panel 25 on which the polarization plates 15, 16, which have different polarization directions, are pasted alternately line by line, and is displayed on the stereoscopic display panel 25. Note that FIG. 4 illustrates a case where both of the video signals for the right eye and the video signals for the left eye are progressive signals. However, when the video signals for the right eye and the video signals for the left eye are interlace signals, the video signals are combined into a signal in which both of the video signals for the right eye and the video signals for the left eye have half the number of vertical lines.

Figure 5:
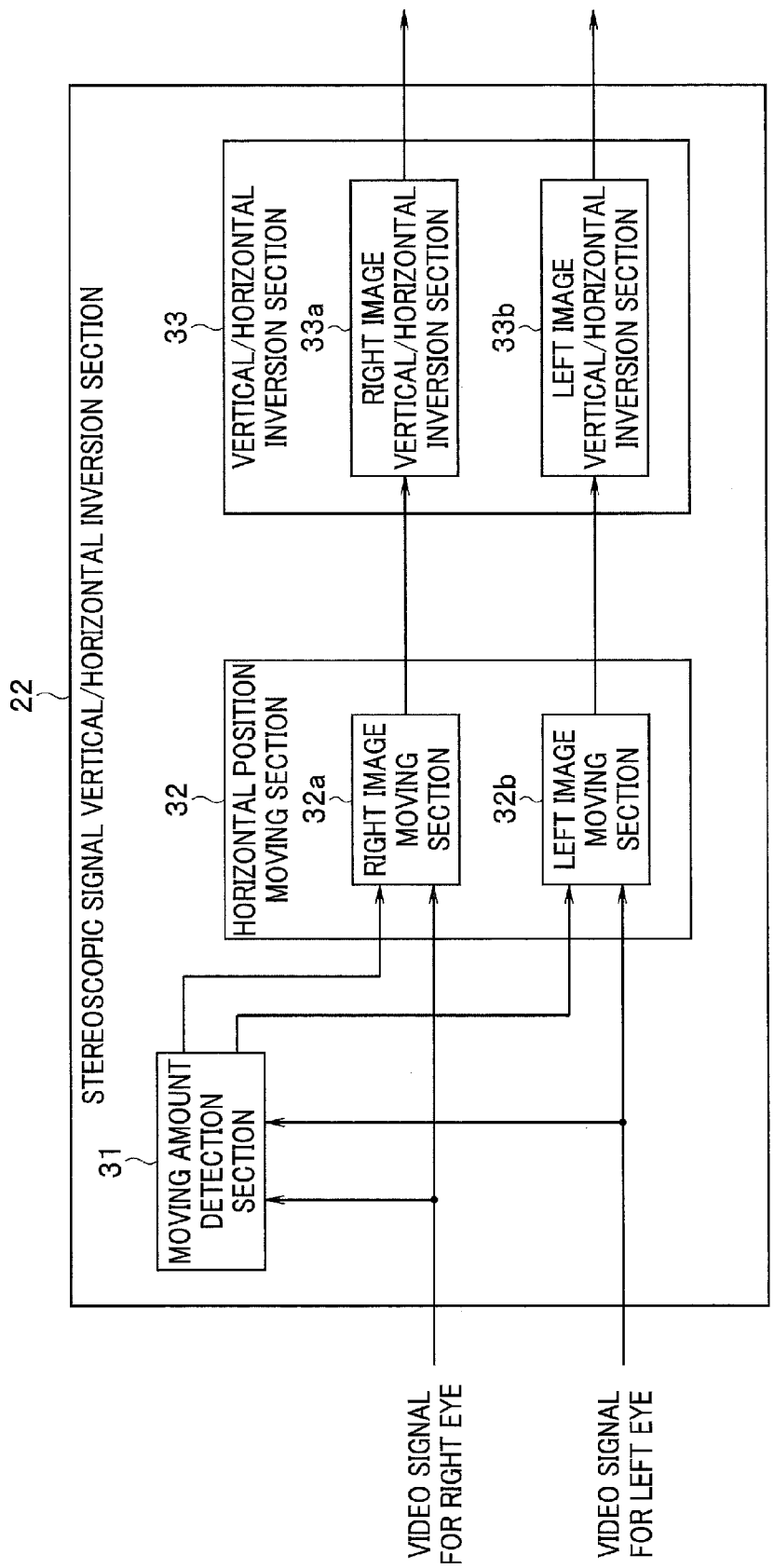
FIG. 5 illustrates a detailed configuration of a stereoscopic signal vertical/horizontal inversion section 22.

Next, description will be made on a detailed configuration of the stereoscopic signal vertical/horizontal inversion section 22. FIG. 5 illustrates the detailed configuration of the stereoscopic signal vertical/horizontal inversion section 22.

As shown in FIG. 5, the stereoscopic signal vertical/horizontal inversion section 22 includes a moving amount detection section 31, a horizontal position moving section 32, and a vertical/horizontal inversion section 33. The horizontal position moving section 32 includes a right image moving section 32a and a left image moving section 32b. In addition, the vertical/horizontal inversion section 33 includes a right image vertical/horizontal inversion section 33a and a left image vertical/horizontal inversion section 33b.

The video signals for the right eye and the video signals for the left eye are inputted to the moving amount detection section 31. The moving amount detection section 31 detects an amount of parallax and depth information of the video signals for the right eye and the video signals for the left eye, by analyzing the inputted video signals for the right eye and video signals for the left eye. The moving amount detection section 31 detects moving amount and moving directions of the respective video signals for the right eye and the video signals for the left eye according to the detected amount of parallax and depth information, and outputs the detected moving amount and moving directions to the right image moving section 32a and the left image moving section 32b of the horizontal position moving section 32. Note that a detailed configuration of the moving amount detection section 31 will be described later.

The moving amount and the moving direction of the video signals for the right eye detected by the moving amount detection section 31 and the video signals for the right eye are inputted to the right image moving section 32a of the horizontal position moving section 32. The right image moving section 32a moves the inputted video signals for the right eye toward the detected moving direction in the horizontal direction by the moving amount of the video signals for the right eye detected by the moving amount detection section 31. The video signals for the right eye, the horizontal position of which has been moved, are inputted to the right image vertical/horizontal inversion section 33a of the vertical/horizontal inversion section 33.

Similarly, the moving amount and the moving direction of the video signals for the left eye detected by the moving amount detection section 31 and the video signals for the left eye are inputted to the left image moving section 32b of the horizontal position moving section 32. The left image moving section 32b moves the inputted video signals for the left eye toward the detected moving direction in the horizontal direction by the moving amount of the video signals for the left eye detected by the moving amount detection section 31. The video signals for the left eye, the horizontal position of which has been moved, are inputted to the left image vertical/horizontal inversion section 33b of the vertical/horizontal inversion section 33.

The right image vertical/horizontal inversion section 33a and the left image vertical/horizontal inversion section 33b vertically and horizontally invert the video signals for the right eye and the video signals for the left eye, the horizontal positions of which have been moved respectively, and output the vertically/horizontally inverted video signals for the right and left eyes to the stereoscopic signal combining section 24 through the selector 23.

Figure 6A:
FIG. 6A illustrates a configuration of a horizontal position moving section 32.
Figure 6B:
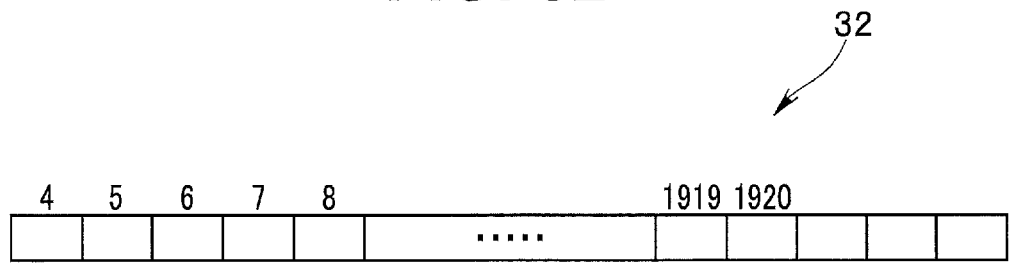
FIG. 6B illustrates the configuration of the horizontal position moving section 32.
Figures 7A, 7B:
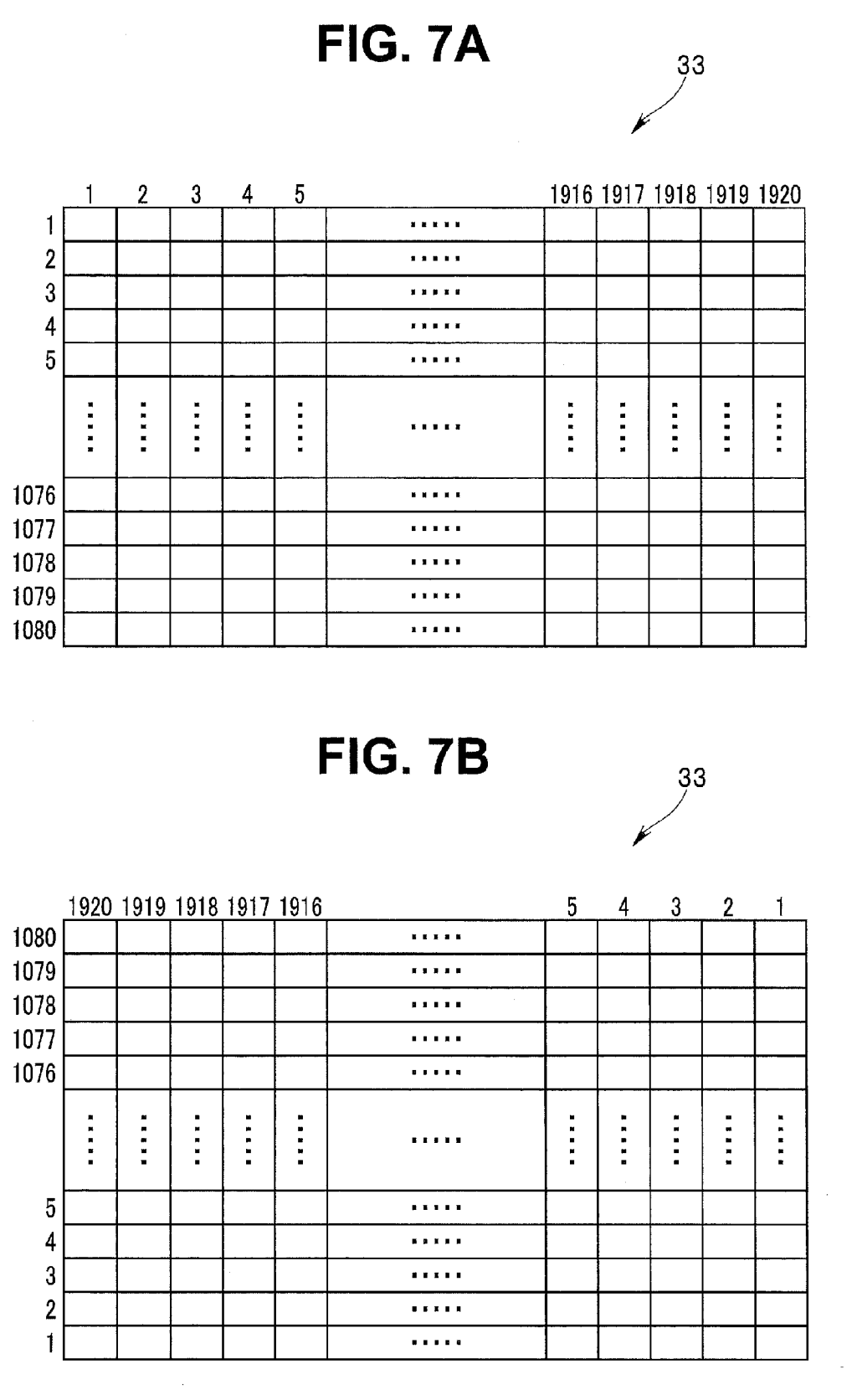

Here, description will be made on the configurations of the horizontal position moving section 32 and the vertical/horizontal inversion section 33. FIG. 6A and FIG. 6B illustrate the configuration of the horizontal position moving section 32. FIG. 7A and FIG. 7B illustrate the configuration of the vertical/horizontal inversion section 33.

As shown in FIG. 6A, the horizontal position moving section 32 is a memory circuit which is configured to be able to store data for one line, i.e., data for 1920 pixels in the present embodiment. The horizontal position moving section 32 changes the read-out position of the data thus stored, to thereby move the horizontal position of the data. Specifically, as shown in FIG. 6B, the horizontal position moving section 32 changes the read-out position such that the data is read out from the fourth pixel, to thereby move the horizontal position in the left direction by three pixels.

In addition, as shown in FIG. 7A, the vertical/horizontal inversion section 33 is a memory circuit which is configured to be able to store data for one frame, i.e., data for 1920 pixels×1080 lines, in the present embodiment. The vertical/horizontal inversion section 33 performs vertical/horizontal inversion by changing the read-out order of the data thus stored. Specifically, as shown in FIG. 7B, the vertical/horizontal inversion section 33 performs vertical/horizontal inversion by changing the read-out order of the stored data to the following order: the 1920th pixel on the 1080 line; the 1919th pixel on the 1080 line; . . . ; and first pixel on the first line, etc.

Note that the horizontal position moving section 32 and the vertical/horizontal inversion section 33 move the horizontal position and perform the vertical/horizontal inversion by changing the read-out position and read-out order of the data stored once, however, the methods of moving the horizontal position and performing the vertical/horizontal inversion are not limited to the same. The horizontal position moving section 32 and the vertical/horizontal inversion section 33 may be configured to move the horizontal position and perform vertical/horizontal inversion by changing the storing position of the data when storing the data, for example. Specifically, when data to be stored at the position of the first pixel on the first line in FIG. 7A is inputted, the data is stored at the position of the 1920th pixel on the 1080 line. Next, when the data to be stored at the position of the second pixel on the first line in FIG. 7A is inputted, the data is stored at the position of the 1919th pixel on the 1080 line. Such processing eliminates the processing of changing the read-out position and read-out order of the data stored once, and enables the data stored once to be used as-is, thereby capable of reducing the processing time for the horizontal position movement and the vertical/horizontal inversion.

Figure 8:
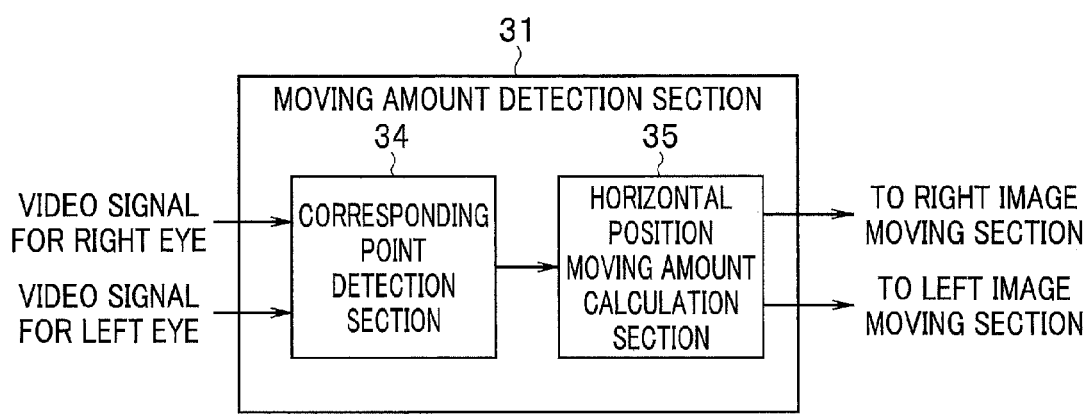
FIG. 8 illustrates a detailed configuration of a moving amount detection section 31.

Next, a detailed configuration of the moving amount detection section 31 will be described. FIG. 8 illustrates the detailed configuration of the moving amount detection section 31.

As shown in FIG. 8, the moving amount detection section 31 includes a corresponding point detection section 34 and a horizontal position moving amount calculation section 35.

The corresponding point detection section 34 identifies the same object included in each of the video signals for the right eye and the video signals for the left eye, from the inputted video signals for the right and left eyes, by performing image recognition based on a color or a shape, to detect the position of the object in the image for the right eye and the position of the object in the image for the left eye. The corresponding point detection section 34 outputs the position information of the object thus detected to the horizontal position moving amount calculation section 35.

The horizontal position moving amount calculation section 35 calculates the moving amount of the horizontal positions of the image for the right eye and the image for the left eye by using the position information of the object outputted from the corresponding point detection section 34. Specifically, the horizontal position moving amount calculation section 35 detects the parallax (gap) between the image for the right eye and the image for the left eye and depth information (near side or far side of the screen) of the image for the right eye and the image for the left eye, based on the position of the object in the image for the right eye and the position of the object in the image for the left eye which are outputted from the corresponding point detection section 34, and calculates the horizontal position moving amount of the respective image for the right eye and image for the left eye based on the detection result.

When the position of the object in the image for the left eye is located on the left side with respect to the position of the object in the image for the right eye, the depth information indicates that the image for the left eye is on the far side of the screen, and when the position of the object in the image for the left eye is located on the right side with respect to the position of the object in the image for the right eye, the depth information indicates that the image for the left eye is on the near side of the screen.

Figure 9A:
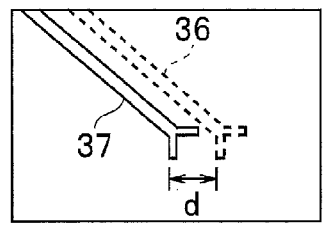
FIG. 9A illustrates moving amount calculation processing in the moving amount detection section 31.
Figure 9B:
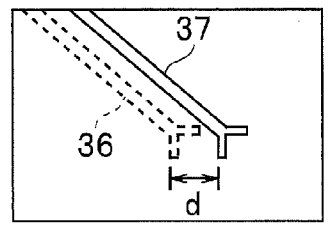
FIG. 9B illustrates the moving amount calculation processing in the moving amount detection section 31.

Now, description will be made on the moving amount calculation processing in the moving amount detection section 31, with reference to FIGS. 9A and 9B. FIGS. 9A and 9B illustrate the moving amount calculation processing in the moving amount detection section 31.

The dotted line in FIG. 9A illustrates the forceps 36 in the image for the right eye, and the solid line in FIG. 9A illustrates the forceps 37 in the image for the left eye. The corresponding point detection section 34 detects the position information of the object, based on the colors and shapes of the forceps 36 in the image for the right eye and the forceps 37 in the image for the left eye. Then, the horizontal position moving amount calculation section 35 detects a parallax d based on the position information of the forceps 36 in the image for the right eye and forceps 37 in the image for the left eye. In addition, since the position of the forceps 37 in the image for the left eye is located on the left side of the forceps 36 in the image for the right eye, the depth information indicates that the position of the forceps 37 is on the far side of the screen.

Before the vertical/horizontal inversion of a stereoscopic video, the depth state is required to be inverted. Therefore, as shown in FIG. 9B, the horizontal positions of the image for the right eye and image for the left eye are moved such that the position of the forceps 36 in the image for the right eye and the position of the forceps 37 in the image for the left eye are switched with each other. Specifically, the horizontal position of the image for the left eye is moved in the right direction by the amount of parallax d, and the horizontal position of the image for the right eye is moved in the left direction by the amount of parallax d. On the other hand, when the depth information indicates that the position of the forceps 37 is on the near side of the screen, the horizontal position of image for the left eye is moved in the left direction by the amount of parallax d, and the horizontal position of the image for the right eye is moved in the right direction by the amount of parallax d.

The horizontal position moving amount calculation section 35 thus calculates the moving amount and moving directions in the horizontal direction of the image for the right eye and image for the left eye, to output the calculated moving amount and moving directions to the horizontal position moving section 32. The horizontal position moving section 32 moves the horizontal positions of the image for the right eye and image for the left eye, based on the moving amount and moving directions in the horizontal direction detected by the moving amount detection section 31. After that, the image for the right eye and the image for the left eye, the horizontal positions of which have been moved, are vertically and horizontally inverted by the vertical/horizontal inversion section 33, and thereby the image for the right eye and the image for the left eye, the depth information of which has not been changed, can be obtained.

Figure 10:
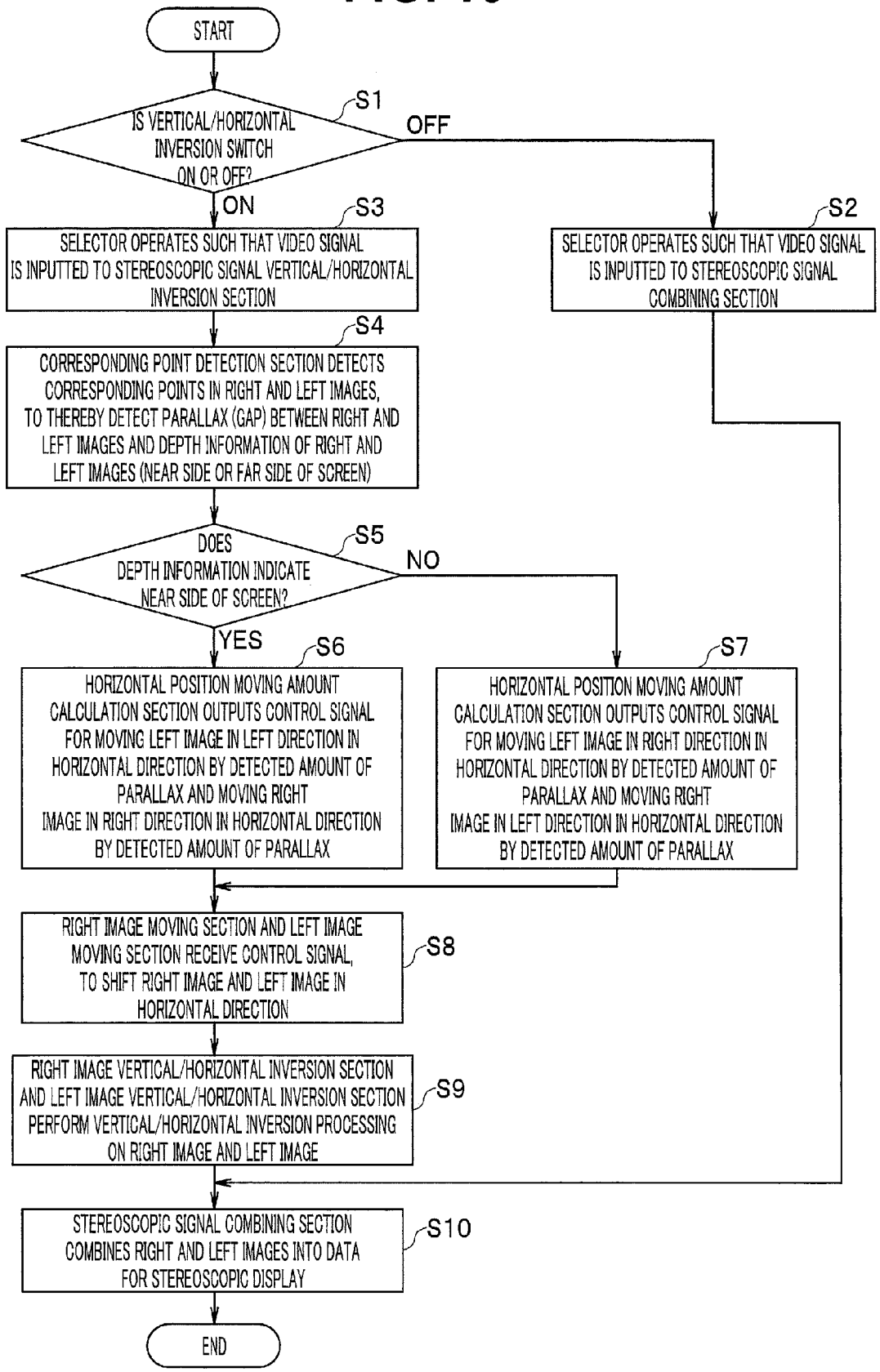
FIG. 10 is a flowchart showing an example of vertical/horizontal inversion processing on the stereoscopic monitor 4.

Next, the vertical/horizontal inversion processing on the stereoscopic monitor 4 will be described with reference to FIG. 10. FIG. 10 is a flowchart showing an example of the vertical/horizontal inversion processing on the stereoscopic monitor 4.

First, it is determined that the vertical/horizontal inversion switch 20a is ON or OFF (step S2). When it is determined that the vertical/horizontal inversion switch 20a is OFF, the selectors 21 and 23 operate such that a video signal is inputted to the stereoscopic signal combining section 24 (step S2). On the other hand, when it is determined that the vertical/horizontal inversion switch 20a is ON, the selector 21 operates such that a video signal is inputted to the stereoscopic signal vertical/horizontal inversion section 22 (step S3). Note that the selector 23 operates such that the output from the stereoscopic signal vertical/horizontal inversion section 22 is inputted to the stereoscopic signal combining section 24.

Next, the corresponding point detection section 34 detects the corresponding points in the right and left images, to thereby detect the parallax (gap) between the right and left images and the depth information of the right and left images (near side or far side of the screen) (step S4), and it is determined whether or not the depth information indicates the near side of the screen (step S5). When it is determined that the depth information indicates the near side of the screen, the process proceeds to "YES", and the horizontal position moving amount calculation section 35 outputs a control signal for moving the left image in the left direction in the horizontal direction and moving the right image in the right direction in the horizontal direction, by the detected amount of the parallax (step S6). On the other hand, when it is detected that the depth information does not indicate the near side of the screen, that is, the depth information indicates the far side of the screen, the process proceeds to "NO", and the horizontal position moving amount calculation section 35 outputs a control signal for moving the left image in the right direction in the horizontal direction and moving the right image in the left direction in the horizontal direction, by the detected amount of the parallax (step S7).

Next, the right image moving section 32a and the left image moving section 32b receive the control signal and cause the right image and the left image to shift in the horizontal direction (step S8), and the right image vertical/horizontal inversion section 33a and the left image vertical/horizontal inversion section 33b perform vertical/horizontal inversion processing on the right image and the left image, respectively (step S9). At last, the stereoscopic signal combining section 24 combines the right and left images into data for stereoscopic display (step S10), and then the processing is terminated.

As described above, the stereoscopic endoscope system 1 detects the parallax between the video signals for the right eye and video signals for the left eye and the depth information, and moves the horizontal positions of the video signals for the right eye and video signals for the left eye based on the detected parallax and depth information. After that, the stereoscopic endoscope system 1 vertically and horizontally inverts the video signals for the right eye and the video signals for the left eye, the horizontal positions of which have been moved. As a result, with the stereoscopic endoscope system 1, the depth information is not inverted as in the case where the video signals for the right eye and the video signals for the left eye are just vertically and horizontally inverted. Therefore, the stereoscopic endoscope system 1 is capable of displaying an accurate stereoscopic video.

The stereoscopic endoscope system according to the present embodiment is capable of observing an accurate stereoscopic video even when the stereoscopic video is vertically and horizontally inverted.

Second Embodiment

Next, the second embodiment will be described.

In the second embodiment, a stereoscopic monitor 4a is used instead of the stereoscopic monitor 4 of the stereoscopic endoscope system 1 according to the first embodiment.

Figure 11:
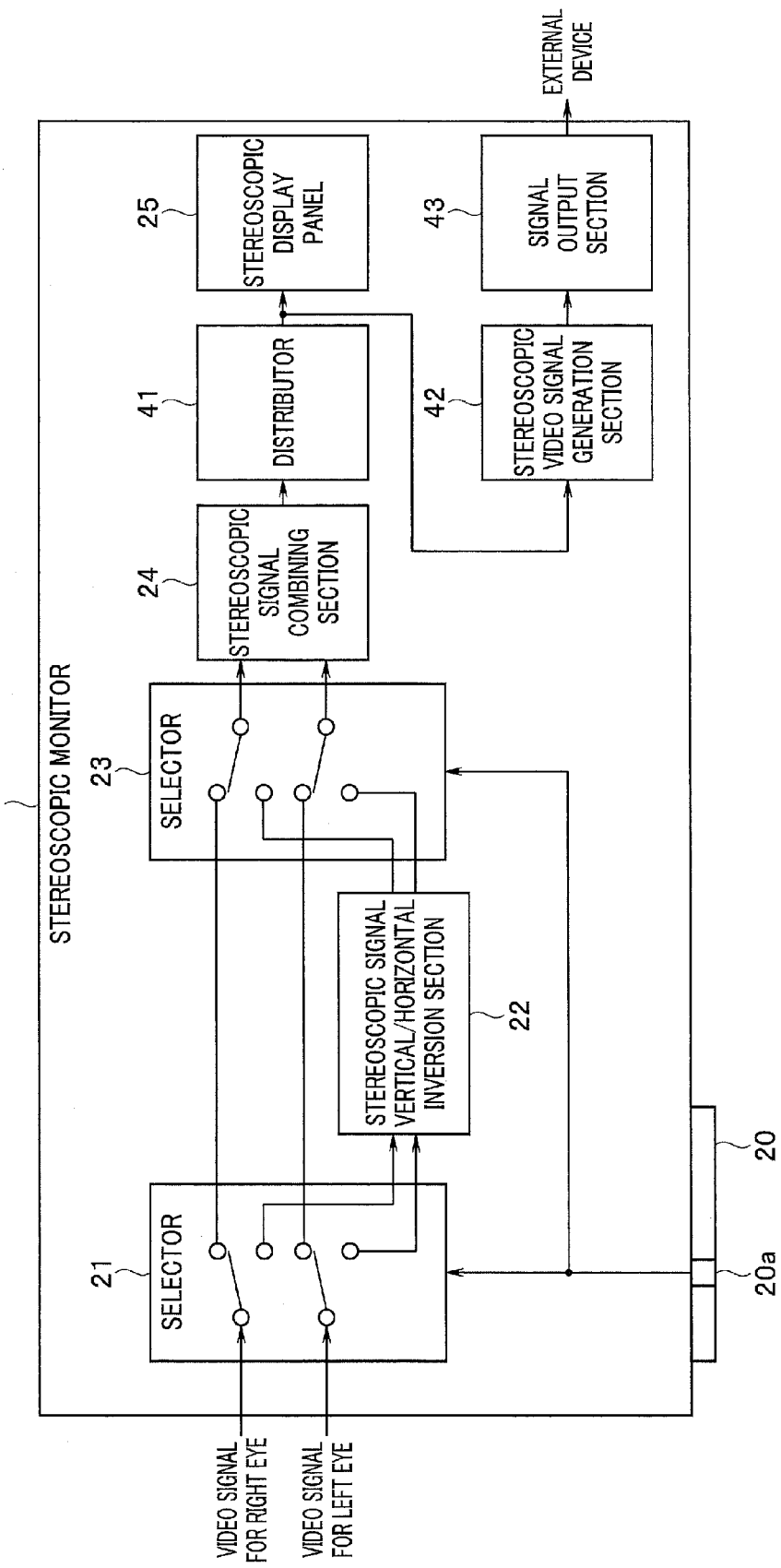
Figure 12:
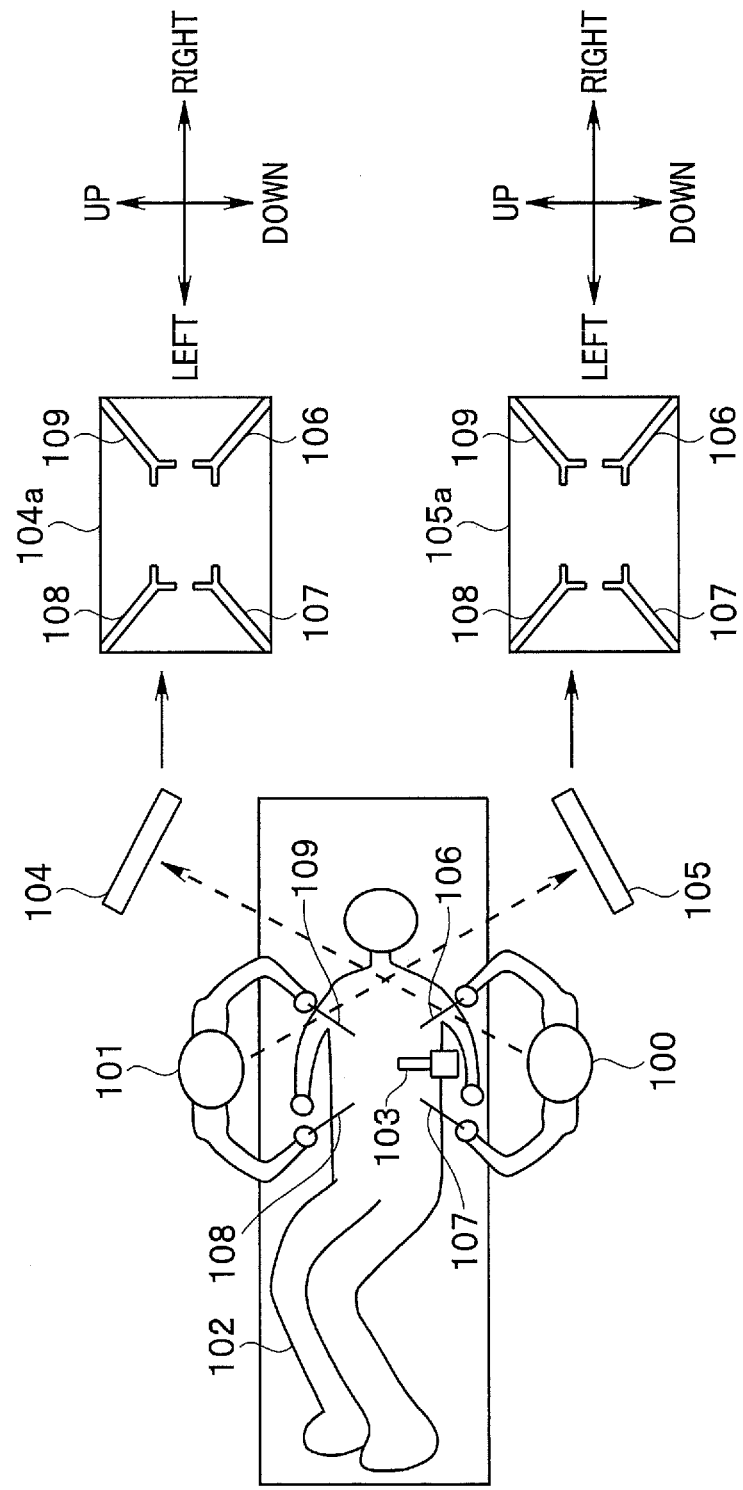
FIG. 12 illustrates an example of a layout of an endoscopic surgery of the chest.

FIG. 11 illustrates a detailed configuration of the stereoscopic monitor 4a. Note that the same constituent elements as those in FIG. 3 are attached with the same reference numerals in FIG. 11 and description thereof will be omitted.

As shown in FIG. 11, the stereoscopic monitor 4a is configured by providing a distributor 41, a stereoscopic video signal generation section 42, and a signal output section 43 additionally to the stereoscopic monitor 4 in FIG. 3. The signal output section 43 is connected with an external device such as a stereoscopic monitor, a recording device, and the like. The distributor 41, the stereoscopic video signal generation section 42, and the signal output section 43 constitute a signal processing system for outputting a stereoscopic video displayed on the stereoscopic monitor 4a in the same state as that of the displayed stereoscopic video and in accordance with the stereoscopic video format compatible with an external device to be connected.

The distributor 41 is provided in a stage preceding the stereoscopic display panel 25, to output the same output signal which is outputted from the stereoscopic signal combining section 24 by distributing the signal into two systems, that is, distributing the signal to the stereoscopic display panel 25 and to the stereoscopic video signal generation section 42. The signal to be displayed is distributed by the distributor 41 immediately before the stereoscopic display panel 25, and thereby capable of extracting the stereoscopic image subjected to image quality adjustment and positional adjustment in the signal processing performed before the distribution.

The stereoscopic video signal generation section 42, as a conversion section, converts the stereoscopic image thus distributed so as to be adjusted to the stereoscopic video format compatible with the external device, and outputs the converted stereoscopic image to the signal output section 43. Specifically, the stereoscopic video signal generation section 42 converts the stereoscopic image into a signal in the side-by-side method or field-sequential method, as a stereoscopic video format, for example, in accordance with the stereoscopic video format compatible with the external device, to output the signal as a result of the conversion to the signal output section 43.

The signal output section 43 converts the signal as a result of the above-described conversion into a video output signal in SDI, DVI, or the like, to output the converted video output signal to the external device.

With the above-described configuration, the stereoscopic endoscope system 1 according to the present embodiment is capable of causing the external device which employs a stereoscopic video format different from the stereoscopic video format employed in the stereoscopic monitor 4a to display or record the stereoscopic video which is same as the stereoscopic video displayed on the stereoscopic monitor 4a.

Note that, regarding the respective steps in the flowchart in the specification, the execution order of the steps may be changed, a plurality of steps may be executed simultaneously, or the execution order of the steps may be changed each time the procedure is executed, as long as the nature of the procedure is not changed.

The present invention is not limited to the above-described embodiments and modified examples, and various changes and modifications are possible without changing the gist of the present invention.

What is claimed is:

1. A stereoscopic endoscope system comprising:
a stereoscopic endoscope that obtains right and left image pickup signals;
a stereoscopic monitor that displays a stereoscopic video corresponding to right and left video signals obtained as a result of predetermined video signal processing performed on the right and left image pickup signals that are obtained with the stereoscopic endoscope;
a corresponding point detection section that detects an amount of parallax and depth information of right and left images by detecting a position of an object in each of an image for the right eye and an image for the left eye based on the inputted right and left video signals;
a horizontal position moving amount calculation section that outputs a control signal for horizontally moving the image for the left eye in a right direction by the amount of parallax and the image for the right eye in a left direction by the amount of parallax when the image for the left eye is on a far side of a screen of the stereoscopic monitor, and for horizontally moving the image for the left eye in the left direction by the amount of parallax and the image for the right eye in the right direction by the amount of parallax when the image for the left eye is on the near side of the screen of the stereoscopic monitor based on the parallax between the image for the right eye and the image for the left eye and depth information of the stereoscopic video, the parallax and the depth information being obtained based on the position in the image for the right eye and the position in the image for the left eye that are outputted from the corresponding point detection section;
a horizontal position moving section that receives the control signal obtained by the horizontal position moving amount calculation section and moves horizontal positions of the right and left video signals, by the amount of parallax, respectively in directions determined according to the depth information;
a vertical/horizontal inversion section that vertically and horizontally inverts the right and left video signals whose horizontal positions have been moved by the horizontal position moving section; and
a stereoscopic signal combining section that combines the right and left video signals subjected to the vertical/horizontal inversion by the vertical/horizontal inversion section, and generates a stereoscopic video signal.

2. The stereoscopic endoscope system according to claim 1, wherein
when the position of the object in the image for the left eye is located on a left side with respect to the position of the object in the image for the right eye, the depth information indicates that the image for the left eye is on the far side of the screen of the stereoscopic monitor, and when the position of the object in the image for the left eye is located on a right side with respect to the position of the object in the image for the right eye, the depth information indicates that the image for the left eye is on the near side of the screen of the stereoscopic monitor.

3. The stereoscopic endoscope system according to claim 1, wherein the stereoscopic monitor includes an output section that outputs the stereoscopic video signal generated by the stereoscopic signal combining section.

4. The stereoscopic endoscope system according to claim 3, wherein the stereoscopic monitor includes a conversion section that is configured to convert the stereoscopic video signal generated by the stereoscopic signal combining section into a stereoscopic video signal which is compatible with an external device connected to the output section and output the stereoscopic video signal obtained by the conversion to the output section.

* * * * *